US012630518B2

(12) United States Patent
Baum et al.

(10) Patent No.: US 12,630,518 B2
(45) Date of Patent: May 19, 2026

(54) PROCESS FOR PREPARING 1,2-BENZISOTHIAZOLINE-3-ONE

(71) Applicant: Thor GmbH, Speyer (DE)

(72) Inventors: Rüdiger Baum, Speyer (DE); Holger Bittermann, Schriesheim (DE); Zhenghao Yang, Jiangsu (CN); Zhang Chaoqiang, Jiangsu (CN); Changhua Zhang, Jiangsu (CN); Qinglin Zheng, Jiangsu (CN); Ashraf Farouk, Landau (DE)

(73) Assignee: Thor GmbH, Speyer (DE)

( * ) Notice: Subject to any disclaimer, the term of this patent is extended or adjusted under 35 U.S.C. 154(b) by 474 days.

(21) Appl. No.: 18/033,943

(22) PCT Filed: Oct. 25, 2021

(86) PCT No.: PCT/EP2021/000131
§ 371 (c)(1),
(2) Date: Apr. 26, 2023

(87) PCT Pub. No.: WO2022/089774
PCT Pub. Date: May 5, 2022

(65) Prior Publication Data

US 2024/0076276 A1 Mar. 7, 2024

(30) Foreign Application Priority Data

Oct. 30, 2020 (EP) .................................... 20000391

(51) Int. Cl.
*C07D 275/04* (2006.01)
*C07C 319/14* (2006.01)

(52) U.S. Cl.
CPC .......... *C07D 275/04* (2013.01); *C07C 319/14* (2013.01)

(58) Field of Classification Search
CPC ............................ C07D 275/04; C07C 319/14
See application file for complete search history.

(56) References Cited

FOREIGN PATENT DOCUMENTS

| | | | |
|---|---|---|---|
| CN | 102491955 | A | 6/2012 |
| CN | 103130738 | A | 6/2013 |
| EP | 0702008 | A2 | 3/1996 |
| WO | WO 2013060766 | A1 | 5/2013 |
| WO | PCT/EP2021/000131 | | 10/2021 |

*Primary Examiner* — Shawquia Jackson
(74) *Attorney, Agent, or Firm* — McCarter & English, LLP

(57) ABSTRACT

The invention relates to a process for preparing 1,2'-benzisothiazoline-3-one according to formula (I), comprising the following steps: (a) reacting a 2-halogenbenzonitrile compound of general formula (II) with a reaction mixture, containing: (i) alkaline sulphide and/or alkaline hydrogen sulphide and (ii) an alkyl halide compound, represented by general formula (III): $R^1X$ (III) for producing an intermediate product of general formula (IV), and (b) reacting the intermediate product of general formula (V) obtained in step (a) with a halogenating agent or an oxidant and subsequent reaction of the 2-(alkylsulfoxy)benzonitrile with an acid to form 1,2-benzisothiazoline-3-one as well as a halide compound of general formula (V) $R^1X$ (V).

13 Claims, No Drawings

PROCESS FOR PREPARING 1,2-BENZISOTHIAZOLINE-3-ONE

CROSS-REFERENCE TO RELATED APPLICATIONS

This application is a 35 U.S.C. § 371 National Stage filing of International Application No. PCT/EP2021/000131, filed on Oct. 25, 2021, which claims priority to European Patent Application 20000391.1, filed on Oct. 30, 2020. The contents of the foregoing applications are incorporated herein by reference.

The invention relates to a process for preparing 1,2-benzisothiazolin-3-one according to formula (I), comprising the steps: (a) reaction of a 2-halobenzonitrile compound of the general formula (II) with a reaction mixture comprising: (i) alkali metal sulfide and/or alkali metal hydrogensulfide and (ii) an alkyl halide compound, represented by the general formula (III): $R^1X$ (III) to form an intermediate of the general formula (IV) and (b) reaction of the intermediate of the general formula (IV) obtained in step (a) with a halogenating agent or an oxidizing agent, and subsequent reaction of the 2-(alkylsulfoxy)benzonitrile with an acid to form the 1,2-benzisothiazolin-3-one and a halide compound of the general formula (V) $R^1X$ (V).

1,2-Benzisothiazolin-3-one is a biocide which is used as a preservative in emulsion paints, varnishes, adhesives, detergents, fuels and in paper manufacturing. In particular, mixtures of 1,2-benzisothiazolin-3-one with 2-methyl-4-isothiazolin-3-one are used for in-can preservation in paints.

The prior art discloses various processes for preparing 1,2-benzisothiazolin-3-one and derivatives thereof.

By way of example, U.S. Pat. No. 4,736,040 describes a process for preparing 1,2-benzisothiazolin-3-ones by reacting 2,2'-dithiobenzamides with an oxygenating agent in the presence of an aqueous alkaline medium. The 2,2'-dithiobenzamides are prepared by nitrosation of anthranilamides and subsequent reaction of the resultant product with sulfur dioxide in the presence of a catalyst. This process for preparing 1,2-benzisothiazolin-3-ones is both time-consuming and costly since many reaction steps are required.

A simpler process for preparing 1,2-benzisothiazolin-3-ones is described in EP 2 687 519. In the process according to EP 2 687 519, a 2-halobenzonitrile is first reacted with an alkyl thiol having 1 to 4 carbon atoms to form a 2-(alkylthio) benzonitrile. The 2-(alkylthio)benzonitrile is then reacted with a halogenating agent in the presence of water in order to obtain the 1,2-benzisothiazolin-3-one. In the context of this process, it is difficult to recycle intermediates, for example the resulting methyl chloride obtained in the preparation of the 1,2-benzisothiazolin-3-one, due to its volatility.

Furthermore, European patent specification EP 2 949 650 B1 discloses a process for preparing BIT by reaction of a 2-halobenzonitrile compound with a thiol compound having 5 to 15 carbon atoms to form a 2-(alkylthio)benzonitrile and subsequent reaction with a halogenating agent in order to obtain the 1,2-benzisothiazolin-3-one. The process disclosed in this publication also has various disadvantages; for example, large amounts of alkyl thioethers that cannot be put to further use are obtained in the described workup of the halide compounds obtained as by-product in the BIT preparation.

The object on which the present invention is based is therefore that of providing an improved process for preparing a 1,2-benzisothiazolin-3-one. The intention is for the process not to have the abovementioned disadvantages of the prior art or only to have them to a significantly lesser extent. The intention is also for the process to be able to be performed in a simpler, more reliable and more cost-effective manner than those described in the prior art.

This object is achieved by a process for preparing 1,2-benzisothiazolin-3-one according to formula (I), (I)

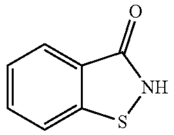

comprising the steps:

(a) reaction of a 2-halobenzonitrile compound of the general formula (II):

(II)

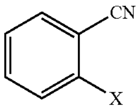

where X is chlorine or bromine;

with a reaction mixture comprising:

(i) alkali metal sulfide and/or alkali metal hydrogensulfide and (ii) an alkyl halide compound, represented by the following general formula (III): $R^1X$ (III), where $R^1$ is selected from the group consisting of unsubstituted or at least monosubstituted $C_1$-$C_{10}$ alkyl, unsubstituted or at least monosubstituted $C_5$-$C_{14}$ aryl and unsubstituted or at least monosubstituted $C_7$-$C_{18}$ aralkyl, where the substituents are selected from the group consisting of F, Cl, Br, I, OH, $NH_2$, $C_1$-$C_8$ alkyl and $OR^2$, where $R^2$ is hydrogen or $C_1$-$C_4$ alkyl; and X is a chlorine or bromine, to form an intermediate of the general formula (IV)

(IV)

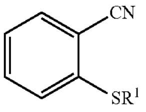

(b) reaction of the intermediate of the general formula (IV) obtained in step (a) with a halogenating agent or an oxidizing agent and subsequent reaction of the 2-(alkylsulfoxy)benzonitrile with an acid to form the 1,2-benzisothiazolin-3-one and a halide compound of the general formula (V) $R^1X$, where $R^1$ is as defined above.

The process according to the invention makes it possible to obtain the 1,2-benzisothiazolin-3-one, starting from the 2-halobenzonitrile compound and using the alkyl halide compound, in a high yield in a particularly economically viable process.

Advantageously, the reaction of the one 2-halobenzonitrile compound according to the general formula (II) with the reaction mixture comprising (i) an alkali metal sulfide and/or alkali metal hydrogensulfide and (ii) the alkyl halide compound according to the general formula (III) results in a significant reduction in the amount of thioethers obtained as by-product compared to the process described in EP 2 949 650 B 1. The process according to the invention also features lower emissions of mercapto compounds compared to the processes described in the prior art.

A third advantage is that the alkyl halide compound which is obtained as by-product in process step (b) can be reused directly and does not have to be first converted into an alkanethiol compound as per the prior art. As a result, the reuse of the alkyl halide compound also becomes more economically viable since the process according to the invention produces significantly smaller amounts of thioether as by-product than the 10% to 25% known from the prior art.

In the first process step (a) of the process according to the invention for preparing 1,2-benzisothiazolin-3-one, a 2-halobenzonitrile compound according to the general formula (II), (II)

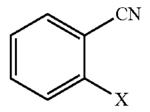

where X is chlorine or bromine, preferably chlorine, is reacted with a reaction mixture comprising:

(i) at least one alkali metal sulfide and/or alkali metal hydrogensulfide and (ii) at least one alkyl halide compound, represented by the following general formula (III): $R^1X$, where $R^1$ is selected from the group consisting of unsubstituted or at least monosubstituted $C_1$-$C_{10}$ alkyl, unsubstituted or at least monosubstituted $C_5$-$C_{14}$ aryl and unsubstituted or at least monosubstituted $C_7$-$C_{18}$ aralkyl, and where the substituents are selected from the group consisting of F, Cl, Br, I, OH, $NH_2$, $C_1$-$C_8$ alkyl and $OR^2$, where $R^2$ is hydrogen or $C_1$-$C_4$ alkyl; and X is chlorine or bromine, in order to obtain the intermediate of the general formula (IV), (IV)

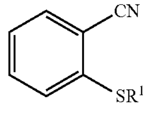

where $R^1$ is as defined above.

According to a preferred embodiment, the 2-halobenzonitrile compound used is 2-bromobenzonitrile and/or 2-chlorobenzonitrile, particularly preferably 2-chlorobenzonitrile.

The 2-halobenzonitrile compound according to the general formula (II) is reacted in process step (a) with (i) the at least one alkali metal sulfide and/or alkali metal hydrogensulfide and (ii) the at least one alkyl halide compound of the general formula (III) to form the intermediate of the general formula (IV).

The alkali metal sulfide and/or alkali metal hydrogensulfide is generally selected from the group consisting of sodium hydrogensulfide, potassium hydrogensulfide, sodium sulfide and potassium sulfide. According to a preferred embodiment of the invention, sodium sulfide is used in process step (a). According to a preferred embodiment of the invention, anhydrous sodium sulfide is used in process step (a). Anhydrous sodium sulfide here means a product having a content of more than 90% by weight, preferably more than 95% by weight, of $Na_2S$. In comparison to hydrated sodium sulfide which has, for example, an $Na_2S$ content of 60% by weight, the use of anhydrous/dry sodium sulfide results in improved yields of 1,2-benzisothiazolin-3-one.

The alkyl halide compound according to the general formula (III): $R^1X$ is generally the compound(s) defined above; preferably, it is compounds of the general formula (III), where $R^1$ is selected from the group consisting of branched or unbranched $C_1$-$C_{10}$ alkyl and X is chlorine or bromine. Particularly preferably, halide compounds are selected from the group consisting of methyl chloride, methyl bromide, ethyl chloride, ethyl bromide, n-propyl chloride, n-propyl bromide, iso-propyl chloride, iso-propyl bromide, n-butyl chloride, n-butyl bromide, sec-butyl chloride, sec-butyl bromide, iso-butyl chloride, iso-butyl bromide, tert-butyl chloride, tert-butyl bromide, n-pentyl chloride, n-pentyl bromide, iso-pentyl chloride, iso-pentyl bromide, sec-pentyl chloride, sec-pentyl bromide, neo-pentyl chloride, neo-pentyl bromide, 1,2-dimethylpropyl chloride, 1,2-dimethylpropyl bromide, iso-amyl chloride, iso-amyl bromide, n-hexyl chloride, n-hexyl bromide, iso-hexyl chloride, iso-hexyl bromide, sec-hexyl chloride, sec-hexyl bromide, n-heptyl chloride, n-heptyl bromide, n-octyl chloride, n-octyl bromide, n-nonyl chloride, n-nonyl bromide, n-decyl chloride, n-decyl bromide. Especially preferred are the halide compounds selected from the group consisting of n-propyl chloride, n-butyl chloride, n-pentyl chloride and n-hexyl chloride.

According to a preferred embodiment of the invention, the halide compound is selected from the group consisting of n-propyl chloride, n-butyl chloride, n-pentyl chloride and n-hexyl chloride. According to a particularly preferred embodiment of the invention, the alkyl halide compound used in process step (a) is n-butyl chloride.

The process according to the invention is preferably characterized in that the halide compound of the general formula (V) obtained in step (b) is at least partially separated from the obtained reaction mixture and fed to process step (a). The return and reuse of the halide compound obtained as by-product in the cyclization is already described in the prior art, for example in EP 2 678 520 A1. The 1,2-benzisothiazolin-3-one is prepared here by cyclization of 2-methylthiobenzonitrile, where, as halide compound, the highly volatile and difficult-to-handle methyl chloride is obtained as by-product.

Evidence for the fact that at the time of filing of the application 1,2-benzisothiazolin-3-one was prepared on an industrial scale by cyclization of 2-methylthiobenzonitrile is provided by analysis of the currently commercially available batches of 1,2-benzisothiazolin-3-one from various manufacturers. As apparent from the table illustrated below, the by-products methyl-1,2-benzisothiazolin-3-one (m-BIT) and methylthiobenzoic acid (MTBA) can be detected in all batches. There were no indications that for example 1,2-benzisothiazolin-3-one was also prepared from 2-butylthiobenzonitrile; the by-product butylthiobenzoic acid was not detectable (n.d.) in any of the batches, the detection limit was 10 ppm.

| Batch No. | Manufacturer | M-BIT [ppm] | MTBA [%] | BTBA [%] |
|---|---|---|---|---|
| #202004063 | Hikal Ltd.[1] | 549 | 0.19 | n.d. |
| #532178 | Hikal Ltd.[1] | 197 | 1.01 | n.d. |
| #202004064 | Dafeng Yuelon[2] | 727 | 0.13 | n.d. |
| #532181 | Dafeng Yuelon[2] | 220 | 1.59 | n.d. |
| #532180 | GBT Limited[3] | 667 | 1.24 | n.d. |
| #532179 | GBT Limited[3] | 520 | 1.44 | n.d. |
| #532177 | Hongkong Hong[4] | 353 | 1.22 | n.d. |
| #538472 | Hongkong Hong[4] | 611 | 936 | n.d. |
| #538606 | Hongkong Hong[4] | 580 | 0.52 | n.d. |
| #538605 | Hongkong Hong[4] | 497 | 1.14 | n.d. |
| #538470 | Hongkong Hong[4] | 524 | 0.27 | n.d. |
| #538471 | Hongkong Hong[4] | 548 | 0.18 | n.d. |
| #507123 | Hongkong Hong[4] | 1622 | 0.24 | n.d. |
| #507125 | Hongkong Hong[4] | 1805 | 0.33 | n.d. |
| #516709 | Hongkong Hong[4] | 609 | 1.55 | n.d. |
| #532175 | Hongkong Hong[4] | 836 | 1.26 | n.d. |
| #532176 | Hongkong Hong[4] | 292 | 1.19 | n.d. |
| #537551 | Hongkong Hong[4] | 304 | 0.0583 | n.d. |
| #537552 | Hongkong Hong[4] | 320 | 0.0525 | n.d. |
| #537652 | Hongkong Hong[4] | 268 | 0.0459 | n.d. |
| #542886 | Linva (Shangh)[5] | 58 | 0.028 | n.d. |
| #542890 | Scale Chemica[6] | 75 | 0.056 | n.d. |
| #543057 | Scale Chemica[6] | 215 | 0.17 | n.d. |
| #543058 | Scale Chemica[6] | 214 | 0.16 | n.d. |
| #555738 | Suzhou Guoxin[7] | 667 | 0.27 | n.d. |
| #555776 | Suzhou Guoxin[7] | 429 | 0.15 | n.d. |
| #555787 | Suzhou Guoxin[7] | 730 | 0.19 | n.d. |

n.d.: The content of BTBA was below the detection limit of 10 ppm.
[1]Hikal Ltd., India;
[2]Dafeng Yuelong, China;
[3]distributor: GBT, manufacturer: Weifang Runan, China;
[4]distributor: Hongkong Hongtai, manufacturer: Shouguang Syntech Fine Chemical Cpo. Ltd, China;
[5]Linva (Shanghai), manufacturer: Shouguang Syntech Fine Chemical Cpo. Ltd, China;
[6]Scale Chemical Corporation, manufacturer: Dalian Biochem, China;
[7]Suzhou Guoxin Group Fengyuan, manufacturer: Lianyungang Sunlion, China.

As already described above, it is possible to use 2-methylthiobenzonitrile in the preparation of 1,2-benzisothiazolin-3-one; however, according to a particularly preferred embodiment of the invention, the alkyl halide compound used in process step (a) is n-butyl chloride. Advantageously, the use of n-butyl chloride in the context of the process according to the invention for preparing 1,2-benzisothiazolin-3-one enables the separation, which is easy to accomplish in terms of process technology, of the butyl chloride from the reaction mixture obtained in process step (b). On account of its boiling point of about 78° C., it can be easily removed and absorbed or recovered, for example by means of distillation from the reaction mixture obtained in process step (b), and at least partially reused in process step (a).

In process step (a), the alkali metal sulfide and/or alkali metal hydrogensulfide is generally used in an amount of 1 to 1.4 mol, preferably in an amount of 1 to 1.2 mol, per mole of 2-halobenzonitrile compound.

Process step (a) is preferably performed in a suitable solvent, which results in a smoother reaction process. The 2-halobenzonitrile compound and the alkali metal sulfide and/or alkali metal hydrogensulfide in this case are preferably initially charged in a reaction vessel in a solvent and the alkyl halide compound, optionally dissolved in a solvent, is added.

The solvent used here may be any non-aqueous organic solvent, as long as it is suitable for the reaction. The usable organic solvents are not subject to any specific restriction and include hydrocarbons, such as n-hexane, n-heptane, cyclohexane, methylcyclohexane, benzene, toulene and xylene; and halogenated hydrocarbons, such as methylene chloride, 1,2-dichloroethane, chlorobenzene and dichlorobenzene. The preferred solvent is chlorobenzene. The amount of the solvent used is normally 1 to 10 times, preferably 1 to 3 times, the weight of the 2-halobenzonitrile.

According to a preferred embodiment of the invention, process step (a) is performed under an inert gas atmosphere, preferably under a nitrogen atmosphere, in a low-water reaction solvent having a water content of less than 10% by weight, based on the reaction solvent. The low water content advantageously results in a relatively high yield of intermediate according to the general formula (IV).

Reaction step (a) is preferably performed in the presence of at least one phase-transfer catalyst that is added to the solvent system in order to promote the reaction. Phase-transfer catalysts that may be used for this purpose are selected from the group consisting of quaternary ammonium salts, quaternary phosphonium salts and crown ethers. Preferred phase-transfer catalysts include quaternary ammonium salts, such as benzyltriethylammonium bromide, benzyltrimethylammonium chloride, hexadecyltriethylammonium bromide, hexadecyltrimethylammonium chloride, dodecyltrimethylammonium chloride, octyltriethylammonium bromide, tetra-n-butylammonium bromide, tetra-n-butylammonium chloride, tetra-n-butylammonium hydrogen sulfate, tetraethylammonium chloride and trioctylmethylammonium chloride; quaternary phosphonium salts, such as hexadecyltriethylphosphonium bromide, hexadecyltributylphosphonium chloride, tetra-n-butylphosphonium bromide, tetra-n-butylphosphonium chloride, trioctylethylphosphonium bromide and tetraphenylphosphonium bromide; and crown ethers such as 18-crown-6, dibenzo-18-crown-6 and dicyclohexyl-18-crown-6. From an economic standpoint, quaternary ammonium salts, such as tetra-n-butylammonium bromide, tetra-n-butylammonium hydrogen sulfate and tetra-n-butylammonium chloride, are preferably usable.

According to a preferred embodiment of the invention, the phase-transfer catalyst is selected from the group of the quaternary ammonium salts, such as tetra-n-butylammonium bromide, tetra-n-butylammonium hydrogen sulfate and tetra-n-butylammonium chloride.

In the case of use of a phase-transfer catalyst, the amount used of the phase-transfer catalyst is usually 0.005 to 0.5 times, preferably 0.01 to 0.2 times, the weight of the 2-halobenzonitrile. If the amount of the phase-transfer catalyst used is less than 0.005 times the weight of the 2-halobenzonitrile, a satisfactory catalytic effect cannot be obtained.

The reaction temperature for the above reaction in process step (a) is normally in the range from 60° C. to 80° C., preferably from 70° C. to 75° C. The reaction time varies with the reaction temperature and the types of phase-transfer catalyst and solvent used, the reactor geometry and the stirring technology used, and cannot be generalized; however, it is normally in the range between 1 and 40 hours.

The 2-halobenzonitrile compound according to the general formula (II) is reacted in process step (a) with (i) the at least one alkali metal sulfide and/or alkali metal hydrogensulfide and (ii) the at least one alkyl halide compound of the general formula (III) to form the intermediate of the general formula (IV). According to a preferred embodiment of the invention, the 2-halobenzonitrile compounds according to the general formula (II) and the alkali metal sulfide and/or alkali metal hydrogensulfide are initially charged in a suitable solvent under an inert gas atmosphere, preferably under a nitrogen atmosphere, and the alkyl halide compound, according to the general formula (III), optionally dissolved in the same solvent, is added. The alkyl halide compound according to the general formula (III) is added over a period of 10 to 40 hours, preferably over a period of 15 to 30 hours. The amount added of the alkyl halide compound is effected either at a constant addition rate or at a variable rate. In the case of the alkyl halide compound being added at a variable rate, a larger amount per unit time is added at the beginning of the reaction than at the end of the reaction.

Continuously adding the alkyl halide compound according to the general formula (III) minimizes the formation of by-products, particularly the formation of thioethers, even further. The loss of alkyl halide compounds through the formation of thioethers can therefore be reduced to below 10%.

After the reaction has ended, the intermediate obtained according to the general formula (IV) may be isolated and purified in the usual manner This may involve washing the reaction mixture for example with water and subjecting the organic phase, once it has been separated off, to a fractional distillation in order to separate the organic solvent and any thioethers formed from the intermediate according to the general formula (IV) present at the bottom, in order to obtain this in the purest possible form.

The present invention also relates to a process for preparing a 2-(alkylthio)benzonitrile compound according to the general formula (IV):

(IV)

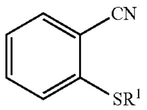

where $R^1$ is as defined above, comprising, in a step (a), the reaction of a 2-halobenzonitrile compound of the general formula (II):

(II)

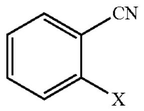

where $R^1$ is as defined above, with a reaction mixture comprising:

(i) alkali metal sulfide and/or alkali metal hydrogensulfide and (ii) an alkyl halide compound, represented by the following general formula (III): $R^1X$ (III), where $R^1$ is as defined above.

In the second process step (b) of the process according to the invention for preparing 1,2-benzisothiazolin-3-one, the intermediate according to the general formula (IV) obtained in process step (a) is reacted or cyclized to form the 1,2-benzisothiazolin-3-one. Such processes are known to those skilled in the art and are described, for example, in EP 2 687 519 A1 and WO 2015/055293 A1, the entire content of which is incorporated herein by reference.

The reaction or cyclization of the intermediate according to the general formula (IV) obtained in process step (a) to form the 1,2-benzisothiazolin-3-one may be effected in different ways:

(b1) with a halogenating agent in the presence of water, or (b2) with an oxidizing agent and subsequent reaction of the 2-(alkylsulfoxy)benzonitrile with an acid to form the 1,2-benzisothiazolin-3-one and a halide compound of the general formula $R^1X$, where $R^1$ is as defined above, and X is chlorine or bromine.

(b1) Cyclization of the Intermediate of the General Formula (IV), the 2-(Alkylthio)Benzonitrile Compound, with a Halogenating Agent to Form 1,2-Benzisothiazolin-3-One In process step (b1), the intermediate of the general formula (IV) obtained in process step (a), the 2-(alkylthio) benzonitrile compound, is reacted with a halogenating agent, preferably in the presence of water, optionally using a reaction solvent, to form a reaction mixture comprising the 1,2-benzisothiazolin-3-one and a halide compound of the general formula (V). The halogenating agent is preferably used here in an amount of about 0.8 to 3 mol and more preferably in an amount of about 1 to 2 mol per mole of 2-(alkylthio)benzonitrile compound. Suitable halogenating agents include chlorine, bromine, sulfuryl chloride and sulfuryl bromide. The halogenating agent used in process step (b1) is preferably chlorine.

Water is preferably used in an amount of about 0.8 to 5 mol and more preferably in an amount of about 1 to 3 mol per mole of the 2-(alkylthio)benzonitrile compound. If the amount of water is outside this range, slight side reactions take place.

The water may be used in the form of an aqueous mineral acid solution by adding a mineral acid to the water. Examples of mineral acids include hydrochloric acid, sulfuric acid and nitric acid. The concentration of the aqueous mineral acid solution may be varied over wide ranges. In the case of hydrochloric acid, the preferred range that is generally used is in the range from 10% by weight to a saturated concentration. In the case of sulfuric acid or nitric acid, 10% to 50% by weight is preferably used. Adding mineral acid to water improves the selectivity during the reaction and suppresses the formation of by-products.

In process step (b1) of the present invention, the use of a reaction solvent is not always necessary; a reaction solvent can be used if required, however.

The solvent used here may be any non-aqueous organic solvent, as long as it is suitable for the reaction. The usable organic solvents are not subject to any specific restriction and include hydrocarbons, such as n-hexane, n-heptane, cyclohexane, methylcyclohexane, benzene, toulene and xylene; and halogenated hydrocarbons, such as methylene chloride, 1,2-dichloroethane, chlorobenzene and dichlorobenzene. The preferred solvent is chlorobenzene. The amount of the solvent used is normally 1 to 10 times, preferably 1 to 2 times, the weight of the 2-(alkylthio) benzonitrile compound.

The reaction step (b1) is optionally performed in the presence of at least one phase-transfer catalyst; the suitable phase-transfer catalysts correspond to those that may be used in process step (a). In the case of use of a phase-transfer catalyst, the amount used of the phase-transfer catalyst is usually 0.005 to 0.5 times, preferably 0.01 to 0.2 times, the weight of the 2-(alkylthio)benzonitrile compound.

The reaction temperature for the cyclization reaction in process step (b1) is normally in the range from 20° C. to 80° C., preferably from 40° C. to 50° C. The reaction time depends on the reaction temperature, the reaction solvent, etc.; generally, it is about 1 to 40 hours.

The 1,2-benzisothiazolin-3-one may be isolated from the reaction mixture obtained by the above process by way of customary crystallization techniques, or by way of recrystallization after extraction. It may also be dissolved in aqueous alkaline solutions and precipitated therefrom. According to a preferred embodiment of the invention, the 1,2-benzisothiazolin-3-one is crystallized by cooling of the reaction mixture, isolated by filtration and optionally washed.

The halide compound obtained in the cyclization and of the general formula $R^1X$, where $R^1$ is as defined above and X is chlorine or bromine, is preferably worked up, or purified and at least partially reused in process step (a).

(b2) Cyclization of the Intermediate of the General Formula (IV), the 2-(Alkylthio)Benzonitrile Compound, with an Oxidizing Agent to Form 1,2-Benzisothiazolin-3-One In process step (b2), the intermediate of the general formula (IV) obtained in process step (a), the 2-(alkylthio) benzonitrile compound, is reacted with an oxidizing agent and subsequent cyclization of the 2-(alkylsulfoxy)benzonitrile with an acid to form the 1,2-benzisothiazolin-3-one and a halide compound of the general formula $R^1X$, where $R^1$ is as defined above and X is chlorine or bromine.

This produces a 2-(alkylsulfoxy)benzonitrile in a first process step starting from the 2-(alkylthio)benzonitrile using at least one peroxo compound.

Peroxo compounds are understood to mean those compounds in which an —O— group is replaced by the —O—O— group. The simplest and preferred representative of this group is hydrogen peroxide ($H_2O_2$). Further representatives of the peroxo compounds are the metal peroxides, particularly the alkali metal and alkaline earth metal peroxides, such as sodium peroxide and potassium peroxide; the peroxohydrates, i.e. the hydrogen peroxide addition compounds with borates, carbonates, urea and phosphates, such as sodium borate peroxohydrate (also called sodium perborate), sodium carbonate peroxohydrate (also called sodium percarbonate), urea peroxohydrate and phosphate peroxohydrate; peroxo acids, such as peroxobenzoic acid, meta-chloroperoxobenzoic acid, peroxophosphoric acid and peroxosulfuric acid. The term "peroxo compounds" is further intended to also include organic peracids, such as peracetic acid, performic acid or perpropionic acid, that are commonly referred to as peroxy compounds. Furthermore, alkyl hydroperoxides, such as tert-butyl hydroperoxide, should also be understood as peroxo compound.

In the preparation of the 2-(alkylsulfoxy)benzonitrile, preference is given to dissolving the 2-(alkylthio)benzonitrile, preferably before the addition of the oxidizing agent, in a carboxylic acid such as acetic acid, formic acid, maleic acid, benzoic acid, meta-chlorobenzoic acid, adipic acid, oleic acid, butyric acid, citric acid and acrylic acid, particularly preferably in acetic acid, formic acid and maleic acid. Sulfuric acid may be added in catalytic amounts in order to accelerate the establishment of equilibrium. Other suitable acids may also be used in addition to the sulfuric acid. Alternatively, peracids may also be used directly as oxidizing agent; however, the in situ production thereof is often simpler.

According to a preferred embodiment of the invention, the peroxo compound is selected from the group consisting of peracetic acid, performic acid, sodium peroxide, potassium peroxide and hydrogen peroxide, particular preference being given to hydrogen peroxide from an economic point of view.

The "a/one peroxo compound" may be either one peroxo compound in pure form or a mixture of multiple peroxo compounds according to the definition above. Preference is given to using peroxo compounds in pure form.

If hydrogen peroxide is used as preferred peroxo compound, it is generally used in the form of a hydrogen peroxide solution. Although the concentration of the peroxide solution is not critical, it is chosen such that as little water as possible is introduced into the reaction medium. In general, use is made of an aqueous hydrogen peroxide solution having at least 20% by weight of $H_2O_2$, preferably one having 50% by weight.

According to one embodiment of the invention, use is made in the context of the preparation of the 2-(alkylsulfoxy)benzonitrile, starting from the 2-(alkylthio)benzonitrile, of an oxidizing agent that is as anhydrous as possible, i.e. that has a water content that is as low as possible. The use of such an oxidizing agent makes it possible to add the amount of water that may be necessary for the further reaction of the 2-(alkylsulfoxy)benzonitrile to form the 1,2-benzisothiazolin-3-one such that the formation of by-products is further minimized, as a result of which the 1,2-benzisothiazolin-3-one can be obtained in even higher yields.

The peroxo compound is normally used in an amount of 0.8 to 1.6 mol, preferably 1.0 to 1.4 mol, per mole of 2-(alkylthio)benzonitrile. If the amount of the peroxo compound is less than 0.8 mol of the 2-(alkylthio)benzonitrile, the amount of unreacted 2-(alkylthio)benzonitrile tends to increase. If, on the other hand, the amount of peroxo compound used exceeds 1.6 mol, side reactions take place, and the yield of 2-(alkylsulfoxy)benzonitrile is significantly reduced.

The process for preparing the 2-(alkylsulfoxy)benzonitrile is characterized in that the reaction is performed in a heterogeneous solvent system in the presence of at least one peroxo compound. The reaction of the 2-alkylthiobenzonitrile used as reactant with the peroxo compound is preferably performed in a two-phase solvent system since the 2-alkylthiobenzonitrile is insoluble in water. In this case, a phase-transfer catalyst is preferably added to the solvent system in order to promote the reaction. Phase-transfer catalysts that may be used for this purpose include quaternary ammonium salts, such as benzyltriethylammonium bromide, benzyltrimethylammonium chloride, hexadecyltriethylammonium bromide, hexadecyltrimethyl ammonium chloride, dodecyltrimethylammonium chloride, octyltriethylammonium bromide, tetra-n-butylammonium bromide, tetra-n-butylammonium chloride, tetra-n-butylammonium hydrogen sulfate, tetraethylammonium chloride and trioctylmethylammonium chloride; quaternary phosphonium salts, such as hexadecyltriethylphosphonium bromide, hexadecyltributylphosphonium chloride, tetra-n-butylphosphonium bromide, tetra-n-butylphosphonium chloride, trioctylethylphosphonium bromide and tetraphenylphosphonium bromide; and crown ethers such as 18-crown-6, dibenzo-18-crown-6 and dicyclohexyl-18-crown-6.

The phase-transfer catalyst is preferably selected from the group of the quaternary ammonium salts, such as tetra-n-butylammonium bromide, tetra-n-butylammonium hydrogen sulfate and tetra-n-butylammonium chloride. According to a particularly preferred embodiment of the invention, the phase-transfer catalyst is tetra-n-butylammonium hydrogen sulfate.

In the case of use of a phase-transfer catalyst, the amount used of the phase-transfer catalyst is normally 0.005 to 0.5 times, preferably 0.01 to 0.2 times, the weight of the 2-alkylthiobenzonitrile. If the amount of the phase-transfer catalyst used is less than 0.005 times the weight of the 2-alkylthiobenzonitrile, an appropriate catalytic effect cannot be obtained. Even if the amount of the phase-transfer catalyst that is used exceeds 0.5 times the weight of the 2-alkylthiobenzonitrile used, no additional effect can be expected and this is therefore not advantageous for economic reasons.

According to a preferred embodiment of the invention, the preparation of the 2-(alkylsulfoxy)benzonitrile may be performed in a solvent. According to an alternative embodiment, however, the preparation may also be effected without the addition of a solvent, only using the components needed for the preparation (2-alkylthiobenzonitrile, water and oxidizing agent).

Solvents used in the process for preparing the 2-(alkylsulfoxy)benzonitrile are not subject to any specific restriction, as long as they are inert with respect to the reaction. Examples of solvents usable in the reaction include hydrocarbons, such as n-hexane, n-heptane, cyclohexane, methylcyclohexane, benzene, toulene and xylene, and halogenated hydrocarbons, such as methylene chloride, 1,2-dichloroethane and chlorobenzene. Chlorobenzene has proven to be particularly preferred in the context of the invention. The amount of the solvent used is normally 1 to 30 times the weight of the 2-(alkylthio)benzonitrile.

In the preparation of the 2-(alkylsulfoxy)benzonitrile, the reaction temperature is normally in the range from 0° C. to 90° C., preferably at temperatures below 50° C. The reaction time varies with the reaction temperature and the reaction solvent and is normally in the range between 1 and 40 hours.

The oxidation of the 2-(alkylthio)benzonitrile as described above is preferably performed in the presence of a catalyst. Useful catalysts here are all catalysts known to those skilled in the art that can be used in the oxidation of alkyl thioethers. This catalyst is preferably selected from the group consisting of phosphonic acids, such as phenylphosphonic acid, tungsten catalysts and molybdenum catalysts, such as $Na_2WO_4$; vanadium catalysts, such as $NaVO_3$, $NH_4VO_3$ and $V_2O_5$; $H_2SO_4$ and titanium complexes. A particularly preferred catalyst is a phosphonic acid or a mixture of multiple phosphonic acids. A very particularly preferred catalyst is a phenylphosphonic acid.

The amount of catalyst used is generally about 0.01 to 10 mol %, preferably about 0.05 to 5 mol %, particularly preferably about 0.1 to 0.5 mol %, based on one mole of 2-(alkylthio)benzonitrile.

The 2-(alkylsulfoxy)benzonitrile prepared in the first process step may be reacted further in the second process step to form the 1,2-benzisothiazolin-3-one with or without prior processing. According to a preferred embodiment, the 2-(alkylsulfoxy)benzonitrile is reacted further to form the 1,2-benzisothiazolin-3-one without further processing.

In the second process step that follows the preparation of the 2-(alkylsulfoxy)benzonitrile, the 1,2-benzisothiazolin-3-one is then prepared starting from a prepared, as described above, 2-(alkylsulfoxy)benzonitrile using at least one acid.

Examples of the acids usable in this process step include all strong acids known to those skilled in the art. The acids may be used both in pure form and in the form of their mixtures. Preference is given to using the acids in pure form.

The acid used here is hydrochloric acid and/or hydrobromic acid. According to a preferred embodiment of the invention, the acid used is hydrochloric acid.

The acid is normally used in an amount of 0.8 to 3.0 mol, preferably 1.0 to 2.0 mol, per mole of 2-(alkylsulfoxy)benzonitrile. The acid may be added in one or multiple stages. According to a preferred embodiment of the invention, 10% of the acid is added in a first stage, and the remainder of the 100% of the acid is added in a second stage. For example, according to this embodiment, 0.1 mole equivalents (acid to benzonitrile) of acid is added at the beginning of the reaction, and the remainder of the 1.0 mole equivalent is added at a later point in time.

Solvents used in the process for preparing the 1,2-benzisothiazolin-3-one starting from the 2-(alkylsulfoxy)benzonitrile are not subject to any specific restriction, as long as they are inert with respect to the reaction. Examples of solvents usable in the reaction include hydrocarbons, such as n-hexane, n-heptane, cyclohexane, methylcyclohexane, benzene, toluene and xylene, and halogenated hydrocarbons, such as methylene chloride, 1,2-dichloroethane, chlorobenzene and dichlorobenzene. Chlorobenzene has proven to be particularly preferred. The amount of the solvent used is normally 1 to 30 times the weight of the 2-(alkylsulfoxy)benzonitrile.

The reaction temperature of the second process step, in the context of which the 1,2-benzisothiazolin-3-one is prepared starting from 2-(alkylsulfoxy)benzonitrile, is usually in the range from 50° C. to 90° C., preferably at temperatures in the range from 70° C. to 80° C. The reaction time varies with the reaction temperature and the reaction solvent and is normally in the range between 1 and 40 hours.

The 1,2-benzisothiazolin-3-one may be isolated from the reaction mixture obtained by the above process by way of customary crystallization techniques, or by way of recrystallization after extraction. It may also be dissolved in aqueous alkaline solutions and precipitated therefrom. According to a preferred embodiment of the invention, the 1,2-benzisothiazolin-3-one is crystallized by cooling of the reaction mixture, isolated by filtration and optionally washed.

The halide compound obtained in the cyclization and of the general formula $R^1X$, where $R^1$ is as defined above and X is chlorine or bromine, is preferably worked up, or purified and at least partially reused in process step (a).

The following example serves to further illustrate the present invention:

Process Step (a): Preparation of 2-(N-Butylthio) Benzonitrile (BTBN) from 2-Chlorobenzonitrile (2-CBN), 1-Chlorobutane and Sodium Sulfide 2-Chlorobenzonitrile (56.2 g, 0.40 mol), coarsely pulverized anhydrous disodium sulfide (93% disodium sulfide content, 40.3 g, 0.48 mol), tetrabutylammonium bromide (3.2 g, 0.01 mol) and chlorobenzene (60.0 g) were mixed in a 500 ml round-bottom flask under a nitrogen atmosphere. The mixture was stirred vigorously at 70° C. to 75° C. (internal temperature). A solution of butyl chloride (39.1 g, 0.42 mol) in chlorobenzene (55.0 g) was slowly added to the mixture at a continuous metering rate of 0.065 g/min, requiring about 24 hours for the complete addition. After the end of the reaction, the reaction mixture was washed with water (200 g) and then with 5% NaCl (100 g) in water and the aqueous phases were discarded. The organic phase was subjected to a distillation under reduced pressure in order to recover the chlorobenzene. The dibutyl sulfide formed as by-product (2.2 g, 0.015 mol) was also removed by distillation in order to obtain the BTBN as pure as possible at the bottom.

Process Step (b): Preparation of 1,2-Benzisothiazolin-3-One (BIT) from 2-(N-Butylthio)Benzonitrile BTBN The BTBN from process step (a) (calculated maximum of 0.39 mol) was transferred into a 500 ml round-bottom flask.

Chlorobenzene (133.0 g), hydrochloric acid (35% by weight, 19.9 g, 0.19 mol of hydrogen chloride, 0.71 mol of water) and tetrabutylammonium bromide (3.2 g, 0.01 mol) were added. The mixture was stirred intensely at 40° C. to 50° C. while chlorine was introduced at a flow rate of 125 ml/min. The content of BTBN was monitored by means of HPLC during the entire process and the chlorination was continued until all BTBN was consumed. The reaction mixture was subsequently stirred for one hour at 70° C., followed by the addition of 150 g of water and heating to 90° C. The 1-chlorobutane was then recovered from the mixture by distillation. After complete distillation and stirring for one hour, the mixture was cooled to ambient temperature.

The colorless crystals obtained were separated off by means of filtration, washed with chlorobezene and water and dried at 50° C. in order to obtain 1,2-benzisothiazolin-3-one. Additional BIT was recovered from the organic layer of the filtrate by extraction with dilute sodium hydroxide solution. The total yield (including solid BIT and aqueous BIT sodium salt), based on 2-CBN, is 90%.

The invention claimed is:

1. A process for preparing 1,2-benzisothiazolin-3-one of formula (I), (I)

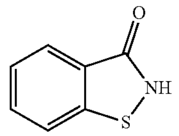

comprising the steps:

(a) reaction of a 2-halobenzonitrile compound of formula (II):

(II)

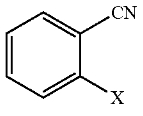

where

X is chlorine or bromine;

with a reaction mixture comprising:

(i) alkali metal sulfide and/or alkali metal hydrogensulfide and (ii) an alkyl halide compound of formula (III): $R^1X$ (III), where $R^1$ is selected from the group consisting of unsubstituted or at least monosubstituted $C_1$-$C_{10}$ alkyl, unsubstituted or at least monosubstituted $C_5$-$C_{14}$ aryl and unsubstituted or at least monosubstituted $C_7$-$C_{18}$ aralkyl, where the substituents are selected from the group consisting of F, Cl, Br, I, OH, $NH_2$, $C_1$-$C_8$ alkyl and $OR^2$, where $R^2$ is hydrogen or $C_1$-$C_4$ alkyl; and X is a chlorine or bromine, to form an intermediate of formula (IV), where $R^1$ is as defined above, (IV)

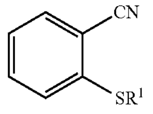

(b) reaction of the intermediate of formula (IV) obtained in step (a) with a halogenating agent or an oxidizing agent and subsequent reaction of the 2-(alkylsulfoxy) benzonitrile with an acid to form the 1,2-benzisothiazolin-3-one and a halide compound of the general-formula (V) $R^1X$ (V), where:

$R^1$ is selected from the group consisting of unsubstituted or at least monosubstituted $C_1$-$C_{10}$ alkyl, unsubstituted or at least monosubstituted $C_5$-$C_{14}$ aryl and unsubstituted or at least monosubstituted $C_7$-$C_{18}$ aralkyl, where the substituents are selected from the group consisting of F, Cl, Br, I, OH, $NH_2$, $C_1$-$C_8$ alkyl and $OR^2$, where $R^2$ is hydrogen or $C_1$-$C_4$ alkyl; and X is chlorine or bromine.

2. The process as claimed in claim 1, characterized in that the alkyl halide compound used in step (a) is butyl chloride.

3. The process as claimed in claim 1, characterized in that the alkali metal sulfide (i) used in step (a) is sodium sulfide ($Na_2S$).

4. The process as claimed in claim 1, characterized in that in process step (b) the intermediate of formula (IV) obtained in step (a) is reacted with a halogenating agent to form a reaction mixture comprising the 1,2-benzisothiazolin-3-one of formula (I) and a halide compound of formula (V).

5. The process as claimed in claim 1, characterized in that in step (b) the halogenating agent is selected from the group consisting of chlorine, bromine, sulfuryl chloride and sulfuryl bromide.

6. The process as claimed in claim 1, characterized in that in process step (b) the intermediate of formula (IV) obtained in step (a) is reacted with a peroxo compound to form 2-(alkylsulfoxy) benzonitrile of the general formula (VI):

(VI)

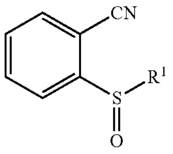

in which $R^1$ is as defined above, and is subsequently reacted with an acid to form the 1,2-benzisothiazolin-3-one of formula (I) and a halide compound of the general formula (V).

7. The process as claimed in claim 1, characterized in that the halide compound of formula (V) obtained in step (b) is at least partially separated from the reaction mixture and fed to process step (a).

8. A process for preparing a 2-(alkylthio) benzonitrile compound of formula (IV):

(IV)

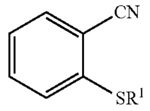

where $R^1$ is selected from the group consisting of unsubstituted or at least monosubstituted $C_1$-$C_{10}$ alkyl, unsubstituted or at least monosubstituted $C_5$-$C_{14}$ aryl and unsubstituted or at least monosubstituted $C_7$-$C_{18}$ aralkyl, where the substituents are selected from the group consisting of F, Cl, Br, I, OH, $NH_2$, $C_1$-$C_8$ alkyl and $OR^2$, where $R^2$ is hydrogen or $C_1$-$C_4$ alkyl, comprising, a step (a), the reaction of a 2-halobenzonitrile compound of formula (II):

(II)

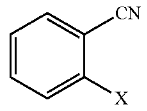

where X is chlorine or bromine, with a reaction mixture comprising:

(i) alkali metal sulfide and/or alkali metal hydrogensulfide and (ii) an alkyl halide compound, of formula (III):

$R^1X$ (III), where $R^1$ and X are as defined above.

9. The process as claimed in claim 1, characterized in that step (a) is performed under an inert gas atmosphere.

10. The process as claimed in claim 1, characterized in that step (a) is performed in the presence of at least one phase-transfer catalyst selected from the group consisting of quaternary ammonium salts, quaternary phosphonium salts and crown ethers.

11. The process as claimed in claim 1, characterized in that in step (a) the 2-halobenzonitrile compound of formula (II) and the alkali metal sulfide and/or alkali metal hydrogensulfide are initially charged and the alkyl halide compound of formula (III) is added.

12. The process as claimed in claim 11, characterized in that the alkyl halide compound of formula (III) is added continuously over a period of 10 to 40 hours.

13. The process as claimed in claim 1, characterized in that step (a) is performed at a temperature in the range from 60° C. to 80° C.

* * * * *